United States Patent [19]
Reetz et al.

[11] Patent Number: 5,817,493
[45] Date of Patent: Oct. 6, 1998

[54] LIPASES IMMOBILIZED IN SOL-GEL PROCESSED HYDROPHOBIC MATERIALS

[75] Inventors: Manfred T. Reetz; Jörg Simpelkamp; Albin Zonta, all of Mülheim an der Ruhr, Germany

[73] Assignee: Studiengesellschaft Kohle MBH, Mulheim an der Ruhr, Germany

[21] Appl. No.: 401,733

[22] Filed: Mar. 9, 1995

[30] Foreign Application Priority Data

Mar. 11, 1994 [DE] Germany ............ 44 08 152.9

[51] Int. Cl.⁶ .................................................. C12N 11/04
[52] U.S. Cl. .................. 435/182; 435/134; 435/135; 435/136; 435/180; 435/181; 435/198
[58] Field of Search .................................. 435/180, 181, 435/182, 198, 134, 135, 136

[56] References Cited

U.S. PATENT DOCUMENTS 4,686,243 11/1987 Keil et al. ............................... 435/182

OTHER PUBLICATIONS

Derwent Japio Abstract 85–164486 J60164486 Seto et al "Method for immobilizing Lipase for ester interchange", Aug. 27, 1985.

Biotech Abs 91–05968 Appl. Biochem. Biotech. Telefoncu et al "Prep. & Charac. of pancreatic lipase immob . . . " (1990)26,3,311–17, Mar. 1990.

Biotech Abs 95–04890 Reetz et al "Angew. Chem. Int. Ed.Engl" (1995) 34,3,301–303, Mar. 1995.

Biotech Abs 95–15425 Kawakami et al Biotech. Tech. (1995) 9, 10, 701–704 "Sol–gel entrapment of lipase . . . ", Sep. 1995.

Hawley's Condensed Chemical Dictionary, Van Norstand Reinhold, New York, 1987, p. 859.

K. Kawakami, et al., Biotechnology Techniques, vol. 8, No. 6, pp. 441–446, (1994).

M–B. Stark, et al., Biotechnology and Bioengineering, vol. 34, pp. 942–950, (1989).

Primary Examiner—Herbert J. Lilling
Attorney, Agent, or Firm—Sprung Kramer Schaefer & Briscoe

[57] ABSTRACT

A process for the preparation of immobilized lipases through reaction on a silica matrix containing non-hydrolyzable organic substituents attached through Si—C bonds.

15 Claims, No Drawings

LIPASES IMMOBILIZED IN SOL-GEL PROCESSED HYDROPHOBIC MATERIALS

The object of the invention are enzyme immobilizates prepared by building a hydrophobic matrix based on silica by sol-gel processing in the presence of lipases, the process of preparing same, and application thereof.

Employing lipases in technical applications meets with increasing interest in hydrolysis or synthesis of esters as well as in transesterification reactions under moderate conditions, inter alia, where hydrophobic substrates are predominantly employed (K. D. Mukherjee, Biocatalysis 1990, 3, 277–293; T. Nielsen, Fette, Seifen, Anstrichmittel 1985, 87, 15–19). Due to their substrate specificity often being broad, lipases are used not only in lipids chemistry but more and more frequently also for stereoselective reactions in organic synthesis. Lipases have also found application in therapeutics. They are used for treatment of digestive insufficiencies caused by pancreatic diseases or cystic fibrosis. An important factor for the economic efficiency of an enzymatic process is a suitable method for the immobilization of the biocatalyst in order to allow ready recovery and multiple use of the enzyme as well as to achieve, if possible, an increase of its stability under the reaction conditions. The prior art in this field of enzyme technology has been summarized several times in review literature, e.g. for lipases (F. X. Malcata, H. R. Reyes, H. S. Garcia, C. G. Hill, Jr., and C. H. Amundson in J. Am. Oil Chem. Soc. 1990, 67, 890–910). In some instances, immobilization by incorporating the lipase in a solid matrix results in an improved activity yield and stability, as compared with other methods, but in most cases is more complicated to perform.

Preparation of $SiO_2$ gels by sol-gel processing (C. J. Brinker, G. W. Scherer, Sol-Gel-Science: The Physics and Chemistry of Sol-Gel-Processing, Academic Press, San Diego 1990; L. L. Hench, J. K. West, Chem. Rev. 1990, 90, 33–72) through hydrolysis of tetraalkoxysilanes, such as tetramethoxysilane or tetraethoxysilane, can be used to incorporate biomolecules in the inorganic matrix. For the immobilization of lipases, however, this method is not suitable since it provides only very unsatisfactory activity yields.

Surprisingly, it has been shown that entrapment of lipases in silicon-containing matrices obtained by hydrolysis of alkoxy-silicon compounds having organic substituents bound to silicon in the presence of appropriate catalysts as well as other additives described hereinafter results in materials with extraordinarily high catalytic activities. Due to immobilization according to our method, unexpected increases of activity by up to two orders of magnitude as compared with the commercially available enzyme preparations employed as well as increases of activity by more than two orders of magnitude as compared with immobilizates prepared by the above-mentioned conventional sol-gel processes (using tetraalkoxysilanes alone) are observed for reactions in organic media. The immobilized lipases prepared according to the method of the invention exhibit excellent stabilities including increased temperature stabilities and have a wide range of applications for reactions in both aqueous and organic media. By varying the parameters of immobilization, the properties of the matrix and of the immobilizates obtained can be controlled, which allows for a wide scope for optimization for a given technical application.

The object of the invention are lipases immobilized in a silica matrix containing organic substituents, and the process of preparing lipases immobilized in this way by hydrolysis of silicon compounds of the type $R_k R''_l Si(OR')_m$ (A) and/or $[(R'O)_n R_o Si]_p X$ (B)

and/or of the type $Y-(R_q R''_r SiO)_s R_q R''_r Si-Y$ (C)

in the presence of an aqueous solution of the lipase and optionally of additional solvents, one (or more) suitable catalyst(s), one or more additives with positive impact on activity, stability, mechanical or magnetic properties of the immobilized biocatalyst obtained, wherein R and R" are selected from a saturated or unsaturated alkyl substituent having 1 to 18 carbon atoms or an aromatic substituent, R' is an alkyl residue having 1 to 5 carbon atoms or an alkali metal atom, X is a bifunctional or higher functional alkyl or aryl residue, or a heteroatom, and Y is —OH, —OR, or —Si(OR')$_3$, k and l are numbers from 0 to 3 (with k+l<4), m is a number from 2 to 4 (with m=4−l−k), n is a number from 1 to 3, o is a number from 0 to 2 (with o=3−n), p is a number from 2 to 4, q and r are numbers from 0 to 2 with q+r=2, and s is a number from 1 to 100.

Preferably used silicon components of the A type with R'=alkyl (e.g. methyl, ethyl) or sodium are:

AI: alkyl or aryltrialkoxysilanes $RSi(OR')_3$ with R=alkyl having a chain length of from $C_1$ to $C_{18}$, alkenyl, e.g. vinyl, or aryl, e.g. phenyl;

AII: dialkyl, alkylaryl or diarylalkoxysilanes $R_k R''_{2-k} Si(OR')_2$ with R, R"=alkyl having chain lengths of from $C_1$ to $C_{18}$, e.g. methyl, wherein compounds of the type AII (with only two groups suitable for cross-linking) may be used in combination with components of the type AI or AIII, e.g. in a molar ratio (AI,AIII):AII of 3–6;

AIII: tetraalkoxysilanes $Si(OR')_4$ in combination with silanes of the type AI, AII, B, or C, the proportion of silicon atoms bearing one or more organic substituents being at least 50% by atoms, based on the total amount of silicon employed.

Silicon components of the B type with R'=alkyl, e.g. methyl or ethyl, are bis(trialkoxysilyl) compounds of the formula $(R'O)_3 Si—X—Si(OR')_3$ with X=alkylene, e.g. $(CH_2)_{2-6}$, arylene, or X=O (use as with AIII in combination with silanes of the type AI, AII, B, or C).

Silicon components of the C type are employed in combination with compounds of the A type, in particular AI and AIII, and are oligomeric or polymeric dialkylsiloxanes, especially polydimethylsiloxane, e.g. with silanol terminal groups and chain lengths of 5–60 monomeric units, the molar ratio A:C of the components being e.g. 3–6.

The silicon compounds of type A and/or B employed may be pre-treated with part of the water with addition of acid or one of the above-mentioned basic catalysts, e.g. by ultrasonic action. The silanes may also be used directly in the enzyme immobilization without a pretreatment step.

The process presented in this invention is widely applicable for a number of lipases of various origins. The immobilized lipases may be of microbial origin, e.g. SP 523 lipase (Novo), or be obtained from bacteria, e.g. of the genus Pseudomonas (e.g. *Ps. fluorescens, Ps. cepacia*), from yeasts of the genus Candida (e.g. *C. antarctica, C. lipolytica*), from molds of the genera Rhizopus (e.g. *Rh. arrhizus, Rh. delemar, Rh. niveus*), Penicillium (e.g. *P. roqueforti*), Aspergillus (e.g. *A. niger*), Mucor (e.g. *M. miehei*), be of plant origin (e.g. from wheat germs), or of animal origin, e.g. from porcine pancreas. An amount of 0.1–30 mg of lipase per mmol of silicon compound(s) is used. Determinations of the protein content in immobilizates without foreign protein added yield a degree of immobilization of 10 to >95%, and the corresponding loadings are 0.2–80 mg of immobilized lipase protein per g of resulting enzyme immobilizate.

The catalysts employed include: basic compounds, e.g. ammonium and alkali metal hydroxides, preferably sodium hydroxide or potassium hydroxide in a stoichiometry of 10–100 mmol per mole of silicon compound(s); ammonia in a stoichiometry of 1–10 mmol per mole of silicon compound (s); ammonium and alkali metal fluorides, preferably sodium fluoride or potassium fluoride in a stoichiometry of 0.1–100, preferably 1–10 mmol per mole of silicon compound(s); and combinations of such compounds.

The following additives are used: (I) proteins (0–200 mg of protein/mg of lipase), e.g. albumin, gelatin, sodium caseinate; (II) polyhydroxy compounds (0–1000 mg of additive/mg of lipase), e.g. poly(vinyl alcohol) (e.g. 0.05–200 mg/mg of lipase), sorbitol, glycerol, polyethyleneglycol (e.g. 0.5–1000 mg/mg of lipase); (III) insoluble organic polymers or inorganic compounds, e.g. magnetite ($Fe_3O_4$), materials based on $SiO_2$, e.g. Celite®, open-pore sintered glasses, such as e.g. Siran®, controlled porous glass (CPG), or kieselguhr; and combinations of such compounds I–III. The type and amount of additives added affect the activity obtained of the immobilized lipase. By addition of suitable additives, significant increases in activity yield can be achieved as compared with analogous systems with no additive.

Water is incorporated in the reaction medium in the form of aqueous solutions of the lipase, of the additives, of the catalyst which are unbuffered or buffered by addition of suitable buffer substances, or else it is incorporated by direct addition, in a stoichiometry of 4–15 mol, preferably 8–12 mol, water per mole of silicon compound(s). Suitable buffer media are e.g. sodium or potassium phosphate buffers with pH values of 6–10. Organic solvents, such as e.g. aliphatic alcohols (e.g. methanol, ethanol, propanol), THF, DMF, may be added to the reaction mixture in small amounts of up to 20% by volume, or the addition of organic solvents can be entirely dispensed with.

A preferred method for immobilizing lipases e.g. comprises adding a buffered or unbuffered aqueous solution of the enzyme to a mixture of water or aqueous buffer, an aqueous solution of the above-mentioned additives I and/or II, and an aqueous solution of the catalyst at temperatures of 0° C.–50° C., preferably at 4° C. to room temperature, mixing by swirling or shaking, adding the silicon compounds (with R'=alkyl), wherein the less reactive components are added first, when components with highly different reaction rates, such as e.g. mixtures of compounds of the types AI and AIII, are used, mixing until a homogeneous phase forms, and swirling or shaking until the reaction mixture gels. If the gelling is accompanied by a significant evolution of heat, the mixture is cooled at 0° C. during and immediately following gelling. The reaction mixture having completely or partially congealed is allowed to stand in a closed vessel, the supernatant, if any, is removed, and the products are dried. The products obtained are generally colorless with properties ranging from brittle to resilient, being hard glassy blocks or fine powders, depending on the silicon components employed. The products obtained may be crushed and used in this form particularly for reactions in a non-aqueous medium. It is preferred, however, to wash the enzyme immobilizate so as to reduce the risk of undesired side reactions or of contamination by excess catalyst and additives and to remove loosely adsorbed, non-enclosed lipase which more easily leaches or deactivates in the reaction and thus leads to reduction of activity in the course of the catalyst's use. To do this, the immobilizates are crushed, shaken with water or aqueous buffer (pH 6–8), filtered off and washed with water and organic solvents, preferably acetone followed by pentane, dried and finally ground.

The materials obtained are mostly white powders having specific surfaces (BET method) of about 0.1–700 $m^2/g$ and pore volumes of about 0.001–1 $cm^3/g$.

In a variant of the process according to the invention, the Si—OH groups capable of condensation with gel formation are not generated by hydrolysis of Si—O-alkyl groups but rather by protonation of Si—O-metal groups. To do this, the pH value of an aqueous solution of an alkyl siliconate, e.g. sodium methylsiliconate, $MeSi(ONa)_3$, is adjusted to pH 6–10 by addition of acids, e.g. hydrochloric acid or acetic acid, and the solution is added to a mixture of enzyme solution and other components mentioned above. Other silicon compounds of the above-mentioned types A, B, and/or C with R'=alkyl can additionally be used for cocondensation in combination with the siliconate solution employed in this variant.

In another variant, the reaction mixture prepared by the above-mentioned processes is poured in excess water prior to gelling and suspended with vigorous stirring. According to this method, the enzyme immobilizate is obtained in the form of approximately spherical particles.

In still another variant, organic polymers or inorganic materials, for instance magnetite ($Fe_3O_4$), oxidic materials based on $SiO_2$, e.g. Celite®, open-pore sintered glasses, such as e.g. Siran®, controlled porous glass (CPG), or kieselguhr, are incorporated as additives of the type III in the immobilizate prepared from silanes together with enzyme solution and the other components mentioned above. The material is added to the reaction mixture either prior to the addition of the silanes or else thereafter, but at any rate before the gelling starts. To place the enzyme immobilizate on large open-pore particles, the reaction mixture is applied to the carrier before the gelling starts. The use of such oxidic additives results in positive characteristics of the immobilizate, e.g. more facile separation of the immobilized catalyst due to the introduction of magnetic properties in the case of magnetite, or in continuous-flow operation by generating a coarse-grained material in the case of porous $SiO_2$ carriers such as Siran®. Generally, the catalytic activity of the immobilizate is not adversely affected as compared to analogous materials without addition of inorganic material, or the activity is even positively affected.

The enzyme immobilizates obtained by the process described in this invention exhibit high activity in esterification and transesterification reactions in organic media. They are generally more active by a factor of 2 to >120 than the same amount of the commercially available enzyme preparations which have been used for the immobilization. For instance, for reactions in an aqueous medium, such as e.g. hydrolysis of olive oil emulsions, activity yields for *Ps. cepacia* lipase of up to 62%, based on the amount of lipase used for the immobilization, are obtained.

The enzyme immobilizate exhibits high stability in water, organic media, or even at elevated temperatures when stored in a dry state. Thus, for instance, virtually no loss in activity (i.e. less than 5%) is observed with *Ps. cepacia* lipase immobilized by the process according to the invention after a storage of three months at room temperature.

I. EXAMPLES:

Example 1 Immobilization of *Ps. cepacia* lipase

Lipase (Amano PS) is suspended in distilled water (25 mg/ml), shaken at room temperature for 15 min, centrifuged, and the supernatant is used for immobilization. In a 2 ml polypropylene vessel, 0.58 ml of water, 0.2 ml of aqueous poly(vinyl alcohol) solution (MW 15,000, Fluka, 4% w/v), 0.1 ml of 1 M NaF, and 0.2 ml of the aqueous enzyme solution (containing 0.46 mg of dissolved protein, corresponding to 5.0 mg of commercially available Amano PS lipase) are mixed, and 0.857 ml of methyltrimethoxysilane (6 mmol, with mol of silane/mol of water (total)=1:10) is added. The two-phase mixture is thoroughly mixed on a vortex shaker for 30 s. After about 30 s and with evolution of heat, the cloudy emulsion has become a clear homogeneous solution which is cooled at 0° C. until the entire reaction mixture congeals to a homogeneous opaque solid after a short period of time. This solid is allowed to stand in a closed vessel at room temperature for 24 h, dried at 30° C. and normal pressure for 3 days, and finally mortar-ground. The raw product is shaken with 10 ml of water at room temperature for 2 h (350 cpm), filtered through a glass frit (D4), and washed with 20 ml of water and then twice with 20 ml of acetone, and 20 ml of pentane. The immobilizate is dried at 30° C. for 24 h and then ball-milled.

Weight obtained: 0.38 g mg of dissolved Amano PS lipase used/g of immobilizate: 1.2 activity factor [activity of immobilizate/(activity of free lipase: 0.55% conversion/h.mg of commercially available lipase)]: 6.3 (test 1)

Example 2 Immobilization of *Ps. cepacia* lipase in gels of the types AI, AI/AI', AI/AII, AI/C, and B

*Ps. cepacia* lipase (Amano PS) is suspended in distilled water (25 mg/ml), shaken at room temperature for 15 min, centrifuged, and the supernatant is used for immobilization. In a 2 ml polypropylene vessel, water (in such an amount that a molar ratio of water (total)/silane(s) of 8:1 is obtained), 0.2 ml of aqueous poly(vinyl alcohol) solution (4% w/v, MW 15,000, Fluka), 0.1 ml of 1M NaF, and 0.2 ml of the aqueous enzyme solution (containing 0.46 mg of dissolved protein, corresponding to 5.0 mg of commercially available Amano PS lipase) are mixed, and the amounts of silicon compounds I and II given in the table are added. The two-phase mixture is thoroughly mixed on a vortex shaker for 30 s and subsequently shaken at room temperature with 1200 cpm. After about 30 s to 3 h and generally with evolution of heat, the onset of gelling occurs. The mixture is cooled at 0° C. until after a short period of time the reaction mixture partially or entirely congeals to an opaque solid which is further treated as described in Example 1.

Stability of the enzyme immobilizates exemplified by the immobilizates 2a and 2g:

residual activity after storage at room temperature for three months: >95% residual activity after storage in 0.1M phosphate buffer, pH 7.0, at room temperature for three months: 31% (2a), 18% (2g)

residual activity after 30 reactions cycles at 30° C. taking 22 h each (batch procedure, esterification of lauric acid with 1-octanol in 2,2,4-trimethylpentane, see activity test I, with the immobilizate being washed after each cycle): >80% (2a, 2g)

residual activity after storage in 1-octanol at 70° C. for 28 days: 65% (2g)

Example 3 Immobilization of *Ps. cepacia* lipase in gels of the types AI/AIII, B/AIII, C/AIII As in Example 2, except that the second silicon compound (II) is tetramethoxysilane (TMOS) in each case.

In all instances, water (in such an amount that the ratio R=moles of water (total)/moles of silane(s) given in the table is obtained), 0.2 ml of aqueous poly(vinyl alcohol) solution (MW 15,000, Fluka, 4% w/v), 0.1 ml of 1M NaF, and 0.4 ml of the aqueous enzyme solution (containing 0.46 mg of dissolved protein, corresponding to 5.0 mg of commercially available Amano PS lipase) are mixed, and the amounts of silicon compounds I and II (TMOS) given in the table are added. The two-phase mixture is thoroughly mixed on a vortex shaker for 30 s (or with mixtures gelling faster until they gel) and subsequently shaken at room temperature with 1200 cpm. After about 2 s to 3 h and generally with evolution of heat, the onset of gelling occurs, whereupon the mixture is cooled at 0° C. Further treatment of the immobilizate is as described in Example 1.

|   | Silane I | Silane II | mmol I | mmol II | Weight obt. (g) | mg lipase/ g gel[d] | Activity factor[b] | Activity (%)[c] | Degree of immob.[d] |
|---|---|---|---|---|---|---|---|---|---|
| a | MTMS | — | 6.0 | — | 0.39 | 1.2 | 4.6 | 6.8 | 0.36 |
| b | MTMS | ETMS | 3.0 | 3.0 | 0.44 | 1.1 | 2.4 | n.d. | 0.45 |
| c | MTMS | DMDES | 4.5 | 0.75 | 0.31 | 1.5 | 4.2 | 9.7 | n.d. |
| d | MTMS | DMDES | 3.0 | 1.5 | 0.31 | 1.5 | 3.7 | n.d. | n.d. |
| e | MTMS | PDMS[e] | 4.5 | 0.75 | 0.49 | 0.9 | 3.4 | 19 | 0.75 |
| f | MTMS | PDMS[e] | 3.0 | 0.75 | 0.30 | 0.15 | 6.3 | 27 | 0.33 |
| g | MTMS | PDMS[e] | 3.0 | 1.0 | 0.28 | 0.17 | 7.5 | n.d. | 0.19 |
| h | MTMS | PDMS[f] | 4.0 | 0.043 | 0.24 | 1.9 | 4.6 | n.d. | 0.39 |
| i | BTMSE | — | 4.0 | — | 0.80 | 0.6 | 1.0 | n.d. | n.d. |
| j | VTMS | — | 6.0 | — | 0.41 | 1.1 | 7.7 | 14 | n.d. |

[a] mg of enzyme protein used/g of immobilizate;
[b] activity test 1 (see page 22), (activity of immobilizate)/(activity of free lipase);
[c] test 2 (see page 23);
[d] (amount of immobilized protein = amount of protein employed - amount of protein in the washings)/(amount of protein employed for immobilization), BCA protein assay, Pierce, BSA standard;
[e] M.W. 400–700;
[f] M.W. 4200;
n.d. = not determined.

| | Silane I | mmol I | mmol TMOS | R | Weight obt. (g) | mg lipase/ g gel[a] | Activity factor[b] | Activity (%)[c] | Degree of Immob.[d] |
|---|---|---|---|---|---|---|---|---|---|
| a | ETMS | 5.0 | 1.0 | 8.0 | 0.46 | 1.0 | 4.5 | 35 | 0.49 |
| b | PTMS | 3.0 | 3.0 | 8.0 | 0.48 | 1.0 | 1.7 | 15 | 0.73 |
| c | PTMS | 5.0 | 1.0 | 8.0 | 0.46 | 1.0 | 6.7 | 21 | 0.43 |
| d | OTMS | 1.5 | 1.5 | 9.3 | 0.32 | 1.4 | 2.4 | n.d. | 0.55 |
| e | ODTMS | 1.5 | 1.5 | 9.3 | 0.46 | 1.0 | 2.5 | 14 | 0.50 |
| f | PDMS[e] | 0.75 | 4.5 | 8.0 | 0.44 | 1.0 | 2.0 | 16 | 0.53 |
| g | PDMS[e] | 0.75 | 3.0 | 8.0 | 0.29 | 1.6 | 5.8 | 62 | 0.19 |
| h | PDMS[e] | 1.0 | 3.0 | 8.0 | 0.27 | 1.7 | 6.2 | 40 | 0.11 |
| i | BTMSH | 3.0 | 0.5 | 8.0 | 0.80 | 0.6 | 1.0 | n.d. | n.d. |
| j | PhTMS | 4.5 | 1.5 | 8.0 | 0.29 | 1.6 | 1.8 | n.d. | n.d. |
| k | PhTMS | 5.0 | 1.0 | 8.0 | 0.22 | 2.1 | 2.2 | n.d. | n.d. |
| l | — | — | 6.0 | 8.0 | 0.49 | 0.9 | 0.03 | 2.3 | 63 |

[a]mg of enzyme protein used/g of immobilizate,
[b]test 1, (activity of the immobilizate)/(activity of commercially available lipase),
[c]test 2,
[d](amount of immobilized protein)/(amount of protein used for immobilization),
[e]M.W. 400–700
abbreviations:
MTMS: methyltrimethoxysilane (Fluka),
ETMS: ethyltrimethoxysilane (ABCR),
PTMS: propyltrimethoxysilane (Aldrich),
OTMS: octyltrimethoxysilane (ABCR),
ODTMS: octadecyltrimethoxysilane (ABCR),
PhTMS: phenyltrimethoxysilane (Fluka),
VTMS: vinyltrimethoxysilane (Fluka),
PDMS: polydimethylsiloxane with silanol terminal groups (ABCR),
BTMSH bis(trimethoxysilyl)hexane (ABCR)

Example 4 Immobilization of *Ps. cepacia* lipase in a gel based on alkyltrimethoxysilane/tetraethoxysilane The same procedure is used as in example 3, except that tetraethoxysilane (TEOS) is used instead of tetramethoxysilane (TMOS). The product is dried and washed as described in example 1.

The same procedure is used as in Example 2a, except that different lipases of different origins (the amounts of commercially available lipase given in the table each in 0.2 ml of 0.1M Na phosphate buffer, pH 7.5, after centrifuging off

| | Silane I | mmol I | mmol TEOS | R | Weight obt (g) | mg lipase/g gel[a] | Activity factor[b] | Degree of immob.[c] |
|---|---|---|---|---|---|---|---|---|
| a | MTMS | 5.0 | 1.0 | 8.0 | 0.46 | 1.0 | 2.1 | 0.50 |
| b | PTMS | 5.0 | 1.0 | 8.0 | 0.48 | 1.0 | 7.1 | 0.55 |
| c | — | — | 6.0 | 8.0 | 0.39 | 1.2 | 0.29 | 0.75 |

[a]mg of enzyme protein used/g of immobilizate,
[b]test 1, (activity of the immobilizate)/(activity of commercially available lipase), (amount of immobilized protein)/(amount of protein used for immobilization)

Example 5 Immobilization of different lipases in gels based on methyltrimethoxysilane insoluble components) are used instead of Amano PS lipase. Gelling time: 0.5–2 min

| | Origin of lipase[a] | U/mg protein[b] | mg lipase[c] | mg soluble lipase proteins | % conv/h-mg[h] | Weight obt.[g] | mg lipase/ g gel[d] | Activity factor[e] | Degree of immob.[f] |
|---|---|---|---|---|---|---|---|---|---|
| a | Rhizopus arrhizus | 1.5 | 35 | 9.1 | 0.10 | 0.39 | 23.3 | 1.6 | 16 |
| b | Rhizopus delemar | 45.6 | 5.0 | 2.8 | 0.1 | 0.39 | 7.2 | 0.4 | 35 |
| c | Rhizopus niveus | 2.6 | 35 | 7.8 | 0.02 | 0.4J | 19.0 | 0.6 | 34 |
| d | Mucor mlehel | 24.2 | 10 | 6.4 | 0.07 | 0.40 | 16.0 | 0.5 | 34 |
| e | Penicllium roqueforti | 1.9 | 10 | 2.8 | 0.07 | 0.38 | 7.4 | 2.B | n.d. |
| f | Candida lipolylica | 30 | 35 | 3.2 | 0.33 | 0.37 | 8.6 | 1.4 | 38 |

-continued

| | Origin of lipase[a] | U/mg protein[b] | mg lipase[c] | mg soluble lipase proteins | % conv/h-mg[h] | Weight obt.[g] | mg lipase/ g gel[d] | Activity factor[e] | Degree of immob.[f] |
|---|---|---|---|---|---|---|---|---|---|
| g | Novo SP 423[g] | ns | 10 | 7.6 | 0.13 | 0.38 | 20.0 | 12.4 | 24 |
| h | wheat germs | 0.12 | 35 | 21.3 | 0.01 | 0.39 | 54.6 | 1.3 | 56 |

[a]Supplied by: Fluka (a, b, c, d, e, f, h), Novo (i);
[b]specification by manufacturer (n.s. = no statement);
[c]commercially available lipase used for immobilization;
[d]mg of soluble enzyme protein used/g of immobilizate;
[e]test 1, (activity of immobilzate)/(activity of commercially available lipase);
[f](amount of immobiliezed protein)/(amount of soluble protein used for immobilization);
[g]recombinant enzyme of unknown microbial origin;
[h]initial rate (% conversion/h · mg of commerically available lipase), activity test 1

Stability of enzyme immobilizates exemplified by immobilizate 4d:
residual activity after storage in 0.1M phosphate buffer, pH 7.0, at room temperature for three months: 70%

Example 6 Immobilization of different lipases in gels based on methyltrimethoxysilane/polydimethylsiloxane The same procedure is used as in Example 2e, except that different lipases of different origins (the amounts of commercially available lipase given in the table, each in 0.2 ml of 0.1M Na phosphate buffer, pH 7.5, after centrifuging off insoluble components) are used instead of Amano PS lipase. Gelling time: 1–5 min Stability of enzyme immobilizates exemplified by immobilizate 5d:
residual activity after storage in 0.1M phosphate buffer, pH 7.0, at room temperature for three months: 92%

Example 7 Immobilization of different lipases in gels based on propyltrimethoxysilane/tetramethoxysilane The same procedure is used as in Example 3c, except that different lipases of different origins (the amounts of commercially available lipase given in the table, each in 0.2 ml of 0.1M Na phosphate buffer, pH 7.5, after centrifuging off insoluble components) are used instead of Amano PS lipase. Gelling time: 0.5–2 min

| | origin of lipase[a] | mg lipase[b] | mg soluble lipase proteins | Weight obt. (g) | mg lipase/g gel[c] | Activity factor[d] | Degree of immob.[e] |
|---|---|---|---|---|---|---|---|
| a | Rhizopus arrhizus | 35 | 9.1 | 0.39 | 23.3 | 4.2 | 20 |
| b | Rhizopus delemar | 5.0 | 2.8 | 0.36 | 1.4 | 0.8 | 59 |
| c | Rhizopus niveus | 35 | 7.8 | 0.32 | 24.4 | 1.4 | 28 |
| d | Mucor miehel | 10 | 6.4 | 0.33 | 194 | 1.9 | n.d. |
| e | Penicilllum rogueforti | 10 | 2.8 | 0.37 | 7.6 | 3.3 | n.d. |
| f | Aspergillus niger | 10 | 9.1 | 0.39 | 23.3 | 21.2 | 88 |
| g | Candida lipolytica | 35 | 3.2 | 0.36 | 8.9 | 1.9 | 66 |
| h | Novo SP 523 | 10 | 7.6 | 0.35 | 21.7 | 19.1 | 88 |
| j | wheat germs | 35 | 21;3 | 0.33 | 64.5 | 2.1 | 42 |

[a]Suppliers and specific activity cf. Example 5;
[b]commerically available lipase used;
[c]mg of soluble enzyme protein used/g of immobilizate;
[d]test 1, (activity of immobilzate)/(activity of commerically available lipase);
[e](amount of immobilized protein)/(amound of soluble protien used for immobilization)

| | origin of lipase[a] | mg lipase[b] | mg soluble lipase proteins | Weight obt. (g) | mg lipase/g gel[c] | Activity factor[d] | Degree of immob.[e] |
|---|---|---|---|---|---|---|---|
| a | Rhizopus arrhizus | 35 | 9.1 | 0.46 | 19.8 | 4.0 | 44 |
| b | Rhizopus delemar | 5.0 | 2.8 | 0.48 | 5.8 | 0.5 | 91 |
| c | Rhizopus niveus | 35 | 7.8 | 0.45 | 17.3 | 1.2 | 59 |
| d | Mucor miehei | 10 | 6.4 | 0.48 | 13.3 | 4.4 | 83 |
| e | Penicillium rogueforfi | 10 | 2.8 | 0.49 | 5.7 | 10.9 | n.d. |
| f | Asperaillus niger | 10 | 9.1 | 0.48 | 18.9 | 18.9 | 95 |
| g | Candida antarctica[f] | 5 | 1.3 | 0.41 | 2.7 | 2.3 | 30 |
| h | Candida lipolytica | 35 | 3.2 | 0.49 | 6.5 | 0.9 | 70 |
| I | Novo SP 523 | 10 | 7.6 | 0.46 | 16.5 | 81.2 | 96 |
| f | wheat germs | 35 | 21.3 | 0.45 | 47.3 | 6.8 | 81 |

-continued

| | origin of lipase[a] | mg lipase[b] | mg soluble lipase proteins | Weight obt. (g) | mg lipase/g gel[c] | Activity factor[d] | Degree of immob.[e] |
|---|---|---|---|---|---|---|---|
| k | porcine pancreas[g] | 35 | 4.0 | 0.49 | 8.2 | 1.1 | 55 |

[a]Suppliers and specific activity cf. Example 5;
[b]commercially available lipase used;
[c]mg of soluble enzyme protein used/g of immobilizate;
[d]test 1, (activity of immobilizate)/(activity of commerically available lipase);
[e](amount of immobilized protein)/(amount of soluble protein used for immobilization);
[f]Fluka, 3.3 U/mg of protein, 0.83% conversion/h · mg of commerically available lipase, activity test 1;
[g]Fluka, 50 U/mg of protein, 0.16% conversion/h · mg of commerically available lipase, activity test 1

Example 8: Immobilization of *Pseudomonas cepacia* lipase

The same procedure is used as in Example 2a, except that the catalysts and amounts of water given below (with a constant value of R=8) have been used instead of 0.1 ml of 1M NaF solution. The gelling time was 0.5–1 min (8a), 24 h (8b, 8c), 48 h (8d). Weights obtained were 0.34–0.42 g mg of dissolved Amano PS lipase used/g of immobilizate: 1.1–1.3

| | Catalyst | ml of water | Activity factor (test 1) |
|---|---|---|---|
| a | 0.1 ml of ammonium fluoride (1M) | 0.364 | 3.2 |
| b | 0.1 ml of sodium hydroxide (1M) | 0.364 | 7.0 |
| c | 0.01 ml of sodium hydroxide (1M) | 0.454 | 8.5 |
| d | 0.1 ml of ammonia solution (1M) | 0.364 | 8.9 |

Example 9: Immobilization of *Ps. cepacia* lipase

As in Example 2a, except that different additives and amounts of water (with a constant ratio R of water:silane= 8:1) as given in the table have been used. Weights obtained were 0.38–0.4 g mg of dissolved Amano PS lipase used/g of immobilizate: 1.1–1.2

| | Additive | ml of water | Activity factor (test 1) |
|---|---|---|---|
| a | 0.2 ml of polyethylene glycol 6000 (Fluka, 20% w/w in water) | 0.364 | 4.7 |
| b | 0.2 ml of bovine serum albumin (Sigma, 50 mg/ml in water) | 0.364 | 5.4 |
| c | 0.1 ml of gelatine (ICN, 4% w/v in water) | 0.464 | 3.5 |
| d | 0.2 ml sorbitol (Merck, 100 mg/ml) | 0.364 | 1.6 |
| e | 0.2 ml of glycerol (Henkel) | 0.564 | 1.7 |
| f | no additive | 0.564 | 1.2 |

Example 10 Immobilization of Novo SP 523 lipase

Lipase SP 523 (Novo) is suspended in distilled water (50 mg/ml), shaken at room temperature for 15 min, centrifuged, and the supernatant is used for immobilization. In a 2 ml polypropylene vessel (Eppendorf), 42 µl of water, 0.1 ml of aqueous poly(vinyl alcohol) solution (MW 15,000, Fluka, 4% w/v), 14 µl of 1M NaF solution, and 0.1 ml of the aqueous enzyme solution (containing 2.06 mg of dissolved protein, corresponding to 5.0 mg of commercially available SP 523 lipase) are mixed, and 0.217 ml of PDMS (0.4 mmol, MW 400–700, ABCR) as well as 0.221 ml of tetramethoxysilane (1.5 mmol, Fluka) are added. The two-phase mixture is thoroughly mixed on a vortex shaker for 2 s, 1.2 g of Siran® (Schott, pretreated with 1 N HCl at 60° C. for 16 h, washed with water, used with a water content of 30%) is added, the mixture is mixed on the vortex shaker for about 5 s until gelling occurs, and cooled at 0° C. for 2 min. The product is dried and washed as described in Example 1, the Siran particles impregnated with the immobilizate are not crushed, however.

Weight obtained: 0.94 g
Loading (SP 523 lipase, mg of dissolved protein used/g of immobilizate): 2.2
Activity yield [test 1]:112
[activity (gel with Siran)]/[activity (same amount of bulk gel without Siran)]:1.9
% of immobilized protein (from determination of protein in the washings): 98

Example 11 Immobilization of *Ps. cepacia* lipase in carriers containing magnetite

*Ps. cepacia* lipase (Amano PS) is suspended in distilled water (25 mg/ml), shaken at room temperature for 15 min, centrifuged, and the supernatant is used for immobilization. In a 2 ml polypropylene vessel (Eppendorf), 0.2 ml of aqueous gelatine solution (4% w/v, ICN), 0.1 ml of 1M NaF, and 0.2 ml of the aqueous enzyme solution (containing 0.46 mg of dissolved protein, corresponding to 5.0 mg of commercially available Amano PS lipase) are mixed, and 0.5 g of magnetite ($Fe_3O_4$, freshly prepared according to Kobayashi et al., J. Coll. Interface Sci. 1991, 141, 505, water content 70%) is added. The mixture is thoroughly mixed on a vortex shaker for 2 s. 0.857 ml (6 mmol) of MTMS is added and the reaction mixture is thoroughly mixed on a vortex shaker until gelling occurs after 0.5–1 min, and subsequently cooled at 0° C. for 1 min. Further treatment of the gel was performed as described in Example 1, except that instead of filtration procedures, decantations with assistance of a permanent magnet were performed.

Weight obtained: 0.47 g
mg of dissolved lipase used/g of immobilizate): 1.0
Activity factor [test 1]:2.2

Example 12 Immobilization of lipases in gels made from sodium methylsiliconate

The amount of commercially available lipase given in the table is suspended in 1 ml of 0.1M Na phosphate buffer, pH 7.0, shaken for 15 min, and liberated from solid residues by centrifugation. Immediately before the immobilization, 0.65 ml of conc. HCl is added with vigorous stirring to 4 ml of sodium methylsiliconate solution (30% in water, 7.5 mmol, ABCR) so that a pH value of 8.0–8.5 results. To a mixture of 0.25 ml of enzyme solution, 0.25 ml of albumin solution (50 mg/ml bovine serum albumin, Sigma), 0.1 ml of 1M sodium fluoride, and 0.5 ml of 1M Na phosphate buffer, pH 7.0, are added 0.5 ml of polydimethylsiloxane (0.9 mmol, MW 400–700, ABCR) followed by 0.5 ml of the sodium siliconate solution (corresponding to 0.8 mmol) and the mixture is thoroughly mixed on a vortex shaker until gelling occurs, i.e. for 1–2 s. Further processing was performed as described in Example 1.

| origin of lipase[a] | mg lipase[b] | mg soluble lipase proteins | Weight obt. (g) | mg lipase/g gel[c] | Activity factor[d] | Degree of immob.[e] |
|---|---|---|---|---|---|---|
| a Pseudomonas fluorescens | 5.0 | 1.3 | 0.15 | 5.7 | 0.8 | 54 |
| b Pseudomonas cepacia | 5.0 | 0.5 | 0.15 | 3.2 | 1.2 | 23 |
| c Rhizopus arrhizus | 20 | 5.2 | 0.14 | 37.3 | 1.7 | 36 |
| d Rhizopus delemar | 2.5 | 1.4 | 0.21 | 6.8 | 2.0 | 43 |
| e Rhizopus niveus | 20 | 4.5 | 0.14 | 32.4 | 5.2 | 80 |
| f Mucor miehei | 5 | 3.2 | 0.13 | 25.2 | 6.2 | 77 |
| g Penicillium rogueforfi | 5 | 1.4 | 0.16 | 8.7 | 5.0 | 62 |
| h Aspergillus niger | 5 | 4.6 | 0.14 | 3.2 | 2.4 | 71 |
| j Candida antarctica | 5 | 1.3 | 0.17 | 7.2 | 0.8 | 51 |
| i Candida lipolytica | 20 | 2.1 | 0.17 | 13.4 | 3.7 | 60 |
| k Novo SP 523 | 5 | 3.8 | 0.17 | 22.6 | 128 | n.d. |
| l wheat germs | 10 | 6.1 | 0.14 | 43.4 | 2.9 | 82 |

[a] Suppliers and specific activity cf. Example 5, Ps. fluorescens lipase: Fluka, 31.5 U/mg of protein;
[b] commercially available lipase used;
[c] mg of soluble enzyme protein used/g of immobilizate;
[d] test 1, (activity of immobilizate)/(activity of commercially available lipase);
[e] (amount of immobilized protein)/(amount of soluble protein used for immobilization);
[f] % conversion/h (initial rate) for the commercially available lipase Example 13 Immobilization of Novo SP 523 lipase 50 mg of SP 523 lipase (Novo) is suspended in 1 ml of 0.1M Na phosphate buffer, pH 7.0, shaken for 15 min, and liberated from solid residues by centrifugation. 0.1 ml of enzyme solution (corresponding to 5 mg of commercially available lipase, 3.8 mg of dissolved protein), 0.2 ml of 1M Na phosphate buffer, pH 7.0, 0.1 ml of poly(vinyl alcohol) (MW 15,000, 4% in water), and 0.04 ml of 1M sodium fluoride solution are mixed and 0.2 ml of polydimethylsiloxane (0.36 mmol, MW 400–700, ABCR) followed by 0.2 ml of sodium methylsiliconate solution (30% in water, 0.38 mmol, ABCR), and 0.03 ml of conc. hydrochlorid acid are added, the mixture is mixed for about 1 s (vortex shaker) and thoroughly mixed with 1 g of Siran® (Schott). The product is dried and washed as described in Example 1, the Siran particles impregnated with the immobilizate are not crushed, however.

Weight obtained: 1.2 g

Loading (lipase, mg of dissolved protein used/g of immobilizate): 3.1

Activity factor [test 1]:187

[activity (gel with Siran)]/[activity (same amount of bulk gel without Siran)]: 1.4

% of immobilized protein (from determination of protein in the washings): 96

Example 14 Immobilization of Ps. cepacia lipase in a MTMS derived sonogel

Ps. cepacia lipase (Amano PS) is suspended in distilled water (25 mg/ml), shaken at room temperature for 15 min, centrifuged, and the supernatant is used for immobilization.

In a 20 ml polypropylene vessel, 4.81 ml methyltrimethoxysilane (MTMS), 1.17 ml distilled water and 0.03 ml 0.001M aqueous NaF solution are mixed and sonicated for 1 h at 0° C. After sonication 0.086 ml 1M aqueous NaF solution, 0.20 ml aqueous poly(vinyl alcoholic)solution (4% w/v), 0.20 ml lipase solution and 0.164 ml dist. water are added to 1.071 ml of MTMS derived sol, which was obtained by sonication.

The mixture is stirred on a vortex shaker (approximately 5 s) and then gently shaken (200 rpm) at room temperature until gelation occurs. The product is dried and washed as described in Example 1.

Weight obtained: 411 mg mg of dissolved Amano PS lipase used/g of immobilisate: 1.1

Activity factor: 7.09

Example 15 Immobilization of Ps. cepacia lipase in a MTMS/PDMS derived aerogel

The same procedure is used as in example 2 (e). After gelation occurs, the gel containing polypropylene vessel is placed in an autoclave (200 ml) and dried with carbon dioxide (approximately 90 g) under supercritical conditions (40° C., 90 bar). After 24 h the immobilizate is washed as described in example 1.

Weight obtained: 0.29 g mg dissolved lipase used/g of immobilisate: 1.5

Activity factor [(activity of the immobilisate)/(activity of commercially available lipase)]=14.1

Degree of immobilization: 0.65

II. Activity Tests and Reactions Using Immobilized Lipases (1) Esterification of lauric acid with 1-octanol To the enzyme immobilizate (100–1000 mg,. depending on the loading) in a 50 ml centrifuge cup (polypropylene, provided with a screw cap) is added a mixture of 100 mg of lauric acid (0.5 mmol, Fluka), 0.158 ml of 1-octanol (1 mmol, Merck), and 2,2,4-trimethylpentane (ad 10 ml, Aldrich), the cup is closed and shaken in a water bath at 30° C. with 180 cpm. To determine the initial rate, samples (0.15 ml) are taken at regular intervals and the ratio of octyl laurate to lauric acid is determined by gas chromatography (0.25 mm FFAP capillary column, 15m). To determine the activity factor, the reaction rate thus determined is divided by the reaction rate that is obtained under the same conditions with such an amount of commercially available enzyme preparation as equals the amount used for immobilization.

(2) Hydrolysis of olive oil emulsions

To 20 ml of a solution of gum arabic (Sigma, 100 g/l in water) is added 6.5 ml of olive oil (Sigma, filtered through alumina B, activity level I), and the mixture is homogenized with a mixer for 30 min. To 25 ml of the substrate emulsion is added 20 ml of 0.1M Na phosphate buffer, pH 9, the pH value is adjusted with 0.1M NaOH to 8.0, and the mixture is homogenized for 2 min. In a 2 ml Eppendorf vessel, 10 mg of the enzyme immobilizate are shaken with 0.1 ml of water for 5 min, 0.9 ml of the buffered substrate emulsion is added, the mixture is thoroughly mixed on a vortex shaker for 5 s, and shaken at 30° C. with 1200 cpm for 0.5–2 h. The reaction is stopped by adding 0.1 ml of a solution of conc. sulfuric acid (1 ml) in hexane/ipropanol 1:5 (10 ml), and the reaction mixture is extracted with 0.6 ml of hexane. To 0.4 ml of the hexane phase, 1 ml of acetone/ethanol 1:1 and phenolphthaleine are added, and the free fatty acid is titrated with 0.1M potassium hydroxide in ethanol. The activity yield is determined by comparing the conversions obtained with the conversion which is obtained with a solution of the free lipase under identical reaction conditions, and is given in percent.

(3) Stereoselective esterifications of racemic secondary alcohols exemplified by the esterification of 1-phenylethanol with acetic anhydride and immobilized *Ps. cepacia* lipase The enzyme immobilizate (immobilized according to Example 2e, its amount depending on the loading) is suspended in 4 ml of benzene, 2.4 µmol of acetic anhydride and 2.4 µmol of racemic 1-phenylethanol are added, and the mixture is shaken at room temperature with 400 cpm. To follow the reaction, samples (0.15 ml) are taken at regular intervals, partitioned with 0.15 ml of 5% $Na_2CO_3$ and after centrifugation, the organic phase is examined by gas chromatography. The enantiomeric excess after completion of the reaction was determined by gas chromatography (0.25 mm capillary, 30 m, column material: 6-t-butyldimethylsilyl-2,3-dimethyl-β-cyclodextrin, 20% in UV1701): Conversion: 50%; %ee (ester):>99 %ee (alcohol) :>99

(4) Transesterification of olive oil with palmitic acid exemplified by immobilized Novo SP523 lipase 0.2 g of palmitic acid are dissolved in 1.5 ml of 2,2,4-trimethylpentane with heating, mixed with 0.2 ml of triolein (Sigma), and the enzyme immobilizate (Novo SP 523 lipase, immobilized according to Example 12, water content 16%, 58 mg, corresponding to 0.15 mg of the soluble lipase protein used for immobilization) is added. The reaction mixture is shaken at 40° C. with 1200 cpm. At regular intervals, samples (0.05 ml) are taken, and the conversion is followed by gas chromatography (following silylation with BSTFA/TMCS (99:1)/pyridine; capillary column with PS048 phase). The activity (defined as the palmitic acid consumption of 1 U=1 µmol/min) is 0.56 U, corresponding to 11.28 U/g of immobilizate.

(5) Hydrolysis of olive oil exemplified by immobilized *Ps. cepacia* lipase

Immobilized *Ps. cepacia* lipase (immobilization method as described above with amounts of enzyme that are sometimes differring; the amount depends on the loading, corresponding to 0.12 mg of lipase protein used for immobilization) is mixed with 10 ml of water and 10 ml of olive oil, and shaken at 40° C. with 230 cpm (50 ml polypropylene vessel provided with a screw cap, 2.7 cm in diameter). At regular intervals, samples of the oil phase (0.15 ml) are taken, acetone/ethanol 1:1 (1 ml) and phenolphthaleine is added, and the liberated fatty acid is titrated with 0.06M KOH in ethanol.

| Immobilizate of: | Loading[a] | v(gel)[b] | v(gel)/v(free) |
|---|---|---|---|
| 2a | 0.75 | 0.26 | 2.1 |
| 2e | 0.44 | 0.26 | 2.1 |
| 3g | 1.1 | 0.15 | 1.2 |
| 3l | 1.5 | 0.31 | 2.4 |

[a]mg of soluble enzyme protein used for immobilization/g of immobilizate obtained;
[b]initial rate (mmol of liberated acid/h)/mg of lipase protein used for immobilizaion, v(free = 0.13 mmol of KOH/h · mg of commerically available lipase

We claim:

1. A process for the preparation of an immobilized lipase, said process comprising entrapping said lipase in a silica matrix formed from an organosilicon compound comprising at least one silicon-carbon bond.

2. The process according to claim 1, wherein said lipase is entrapped in said silica matrix by sol-gel processing of said organosilicon compound in the presence of said lipase.

3. The process according to claim 1, wherein the process is conducted in the presence of at least one catalyst and optionally in the presence of at least one additive.

4. The process according to claim 1, wherein the organosilicon compound has a formula selected from the group consisting of $R_kR''_lSi(OR')_m$ (A), $[(R'O)_nR_oSi]_pX$ (B) and $Y—(R_qR''_rSiO)_sR_qR''_rSi—Y$ (C), in which R and R'' are selected from the group consisting of saturated or unsaturated hydrocarbon groups having 1 to 18 carbon atoms or aromatic groups, R' is an alkyl residue having 1–5 carbon atoms or an alkali metal atom, X is a bifunctional or higher functional alkyl or aryl residue, and Y is —OH, —OR or —Si(OR')$_3$, k and l are numbers from 0 to 3 (with k+1<4), m is a number from 2 to 4 (with m=4–l–k), n is a number from 1 to 3, o is a number from 0 to 2 (with o=3–n), p is a number from 2 to 4, q and r are numbers from 0 to 2 with q+r=2, and s is a number from 1 to 100.

5. The process according to claim 4, wherein the organosilicon compound has formula A in which R'=alkyl or sodium.

6. The process according to claim 4, wherein the organosilicon compound has formula B in which R'=alkyl, and X=alkylene or arylene.

7. The process according to claim 4, wherein the organosilicon compound has formula C, and the organosilicon compound of formula C is used in combination with an organosilicon compound of formula A to form the matrix to entrap the lipase.

8. The process according to claim 5, wherein the organosilicon compound of formula A has the formula RSi(OR')$_3$ AI, wherein R=alkyl having chain lengths of from $C_1$ to $C_{18}$, alkenyl or aryl, and R'=alkyl or sodium.

9. The process according to claim 5, wherein the organosilicon compound of formula A has the formula $R_kR''_{2-k}Si(OR')_2$ AII, wherein R, R''=alkyl having chain lengths of from $C_1$ to $C_{18}$, and R'=alkyl or sodium, and the organosilicon compound of formula AII is used in combination with an organosilicon compound of formula AI to form the matrix to entrap the lipase.

10. The process according to claim 5, wherein the organosilicon compound of formula A has the formula Si(OR')$_4$ AIII, wherein R'=alkyl or sodium, and the organosilicon compound of formula AIII is used in combination with an organosilicon compound of formula AI, AII, B or C to form the matrix to entrap the lipase, and wherein the proportion of silicon atoms having silicon-carbon bonds in said matrix is at least 50% by atoms, based on the total amount of silicon atoms employed in said matrix.

11. The process according to claim 6, wherein the organosilicon compound of formula B is used in combination with an organosilicon compound of formula AI, AII, or C, or with a second organosilicon compound of formula B having a different X value to form the matrix to entrap the lipase.

12. The process according to claim 3, wherein the catalyst is a basic compound selected from the group consisting of ammonium and alkali metal hydroxides, ammonia, ammonium, alkali metal fluorides, and mixtures thereof.

13. The process according to claim 3, wherein an additive is added, and the additive is selected from the group consisting of proteins, polyhydroxy compounds, insoluble organic polymers, or inorganic compounds.

14. The process according to claim 13, wherein the additive is selected from the group consisting of albumin, gelatin, sodium caseinate, poly(vinyl alcohol), sorbitol, glycerol, polyethylene glycol, magnetite ($Fe_3O_4$), Celite, open-pore sintered glasses, silica gel, and diatomaceous earth.

15. Immobilized lipase produced by the process according to claim 1.

* * * * *